US009808573B1

(12) United States Patent
Dooley

(10) Patent No.: US 9,808,573 B1
(45) Date of Patent: Nov. 7, 2017

(54) ORGANIZATIONAL SYSTEM FOR MEDICAL VENOUS ACCESS LINES

(71) Applicant: Barron Dooley, Hillsboro, OR (US)

(72) Inventor: Barron Dooley, Hillsboro, OR (US)

(73) Assignee: Busara Technologies, LLC, Beaverton, OR (US)

( * ) Notice: Subject to any disclaimer, the term of this patent is extended or adjusted under 35 U.S.C. 154(b) by 0 days.

(21) Appl. No.: 15/393,538

(22) Filed: Dec. 29, 2016

Related U.S. Application Data

(60) Provisional application No. 62/310,142, filed on Mar. 18, 2016.

(51) Int. Cl.
| | |
|---|---|
| A61M 5/14 | (2006.01) |
| A61M 39/00 | (2006.01) |
| F16L 3/10 | (2006.01) |
| F16L 3/223 | (2006.01) |
| A61B 50/33 | (2016.01) |

(52) U.S. Cl.
CPC .......... *A61M 5/1418* (2013.01); *A61B 50/33* (2016.02); *A61M 5/1415* (2013.01); *A61M 39/00* (2013.01); *F16L 3/2235* (2013.01)

(58) Field of Classification Search
CPC .. A61M 5/1418; A61M 5/1415; A61M 5/141; A61M 39/00; A61B 50/33; F16L 3/2235; F16L 3/1091
USPC .... 604/174, 207, 111; 248/68.1, 681, 316.7, 248/689, 690; 128/849
See application file for complete search history.

(56) References Cited

U.S. PATENT DOCUMENTS

| | | | | |
|---|---|---|---|---|
| 4,794,441 A | * | 12/1988 | Sugawara | H03K 17/567 257/124 |
| 4,971,271 A | * | 11/1990 | Sularz | F16L 3/223 248/229.13 |
| 5,224,674 A | * | 7/1993 | Simons | A61M 5/1418 248/68.1 |
| 5,334,186 A | * | 8/1994 | Alexander | A61M 5/1418 128/DIG. 15 |
| 5,389,082 A | * | 2/1995 | Baugues | A61M 5/1418 128/DIG. 26 |
| 5,464,025 A | * | 11/1995 | Charles | A61B 46/23 128/849 |
| 5,651,775 A | * | 7/1997 | Walker | A61M 5/31533 604/207 |
| 6,858,104 B2 | * | 2/2005 | Flanagan | B23K 26/03 156/272.8 |
| 9,033,154 B2 | * | 5/2015 | DeVore | A61B 19/026 206/370 |

(Continued)

*Primary Examiner* — Tan Le
(74) *Attorney, Agent, or Firm* — Plager Schlack LLP

(57) ABSTRACT

A device for securing and organizing tubing, such as medical venous access lines, includes a tray; a fastener attached to the tray, the fastener designed to attach the tray to another object, such as a post from an IV unit or a patient's bed; at least one tube slot built into the tray, the tube slot sized to accommodate a portion of a tube; a first strap attached to the tray proximate to the fastener; and a second strap attached to the tray proximate to the end of the tray distal from the fastener, wherein the first strap and the second strap are designed to secure the tube within the tube slot without impeding flow through the tube. The device may further include label tabs extending upwardly from the tray proximate to each tube slot.

7 Claims, 4 Drawing Sheets

(56) References Cited

U.S. PATENT DOCUMENTS

2009/0105656 A1\* 4/2009 Schaeffer .............. A61M 25/02
                                                    604/174
2015/0144746 A1\* 5/2015 Stewart ............... A61M 5/1418
                                                    248/67.5

\* cited by examiner

ORGANIZATIONAL SYSTEM FOR MEDICAL VENOUS ACCESS LINES

RELATED APPLICATION

This application claims priority to provisional patent application U.S. Ser. No. 62/310,142 filed on Mar. 18, 2016 entire contents of which is herein incorporated by reference.

BACKGROUND

The embodiments herein relate generally to medical devices, and more particularly, to an organizational system for medical venous access lines.

Existing medical intravenous line systems merely drape the line/lines over a nearby object, such as the patient's bed or an IV stand. Moreover, medical providers do not currently systematically categorize and hold a patient's IV lines, which requires a medical provider to sort through the multiple lines and track back to the treatment source, such as a fluid bag, to identify which treatment goes with each line. Because of the lack of an organizational system, the IV lines are prone to being pulled and to collecting dirt from the floor.

Therefore, what is needed is a device for organizing and securing medical venous access lines to prevent or lessen the likelihood of pulling and to improve efficiency of determining which line corresponds with which treatment.

SUMMARY

Some embodiments of the present disclosure include a device for securing and organizing tubing, such as medical venous access lines, includes a tray; a fastener attached to the tray, the fastener designed to attach the tray to another object, such as a post from an IV unit or a patient's bed; at least one tube slot built into the tray, the tube slot sized to accommodate a portion of a tube; a first strap attached to the tray proximate to the fastener; and a second strap attached to the tray proximate to the end of the tray distal from the fastener, wherein the first strap and the second strap are designed to secure the tube within the tube slot without impeding flow through the tube. The device may further include label tabs extending upwardly from the tray proximate to each tube slot.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to organize and secure medical venous access lines and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Fastener
2. Tray

The various elements of the device of the present disclosure may be related in the following exemplary fashion. It is not intended to limit the scope or nature of the relationships between the various elements and the following examples are presented as illustrative examples only.

Figure 1:
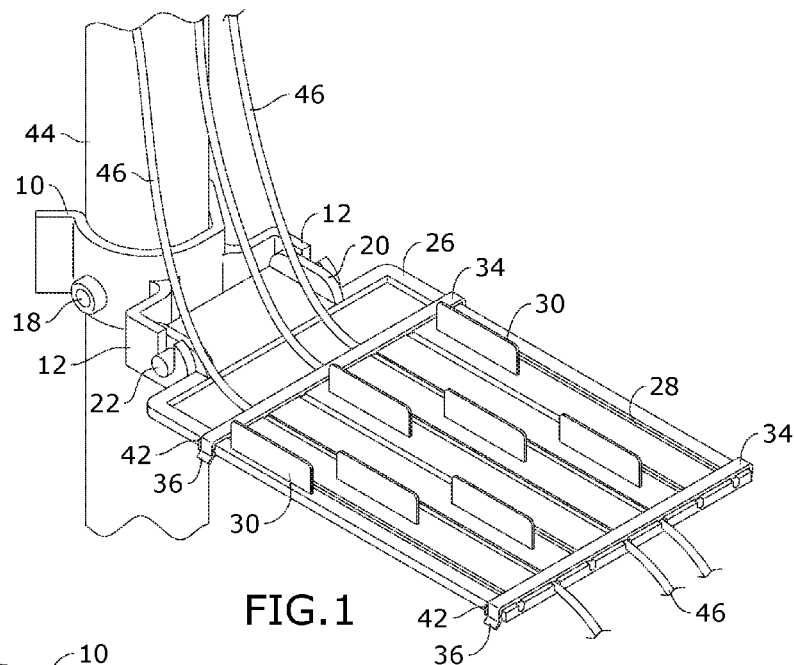
FIG. 1 is a perspective view of one embodiment of the present disclosure, shown in use.
Figure 2:
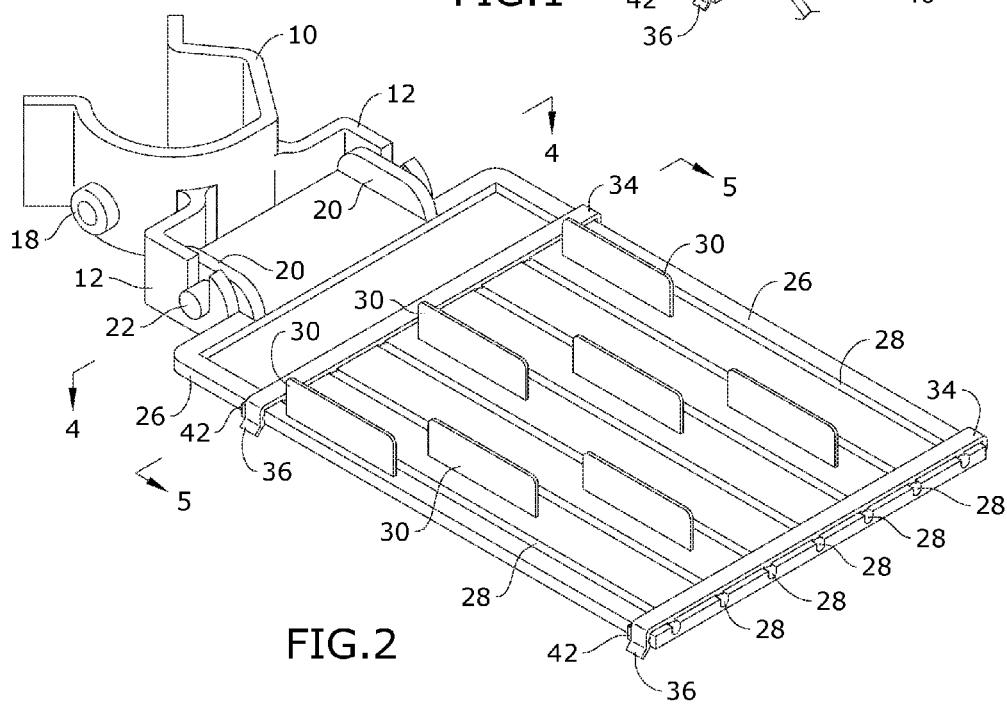
FIG. 2 is a perspective view of one embodiment of the present disclosure.
Figure 3:
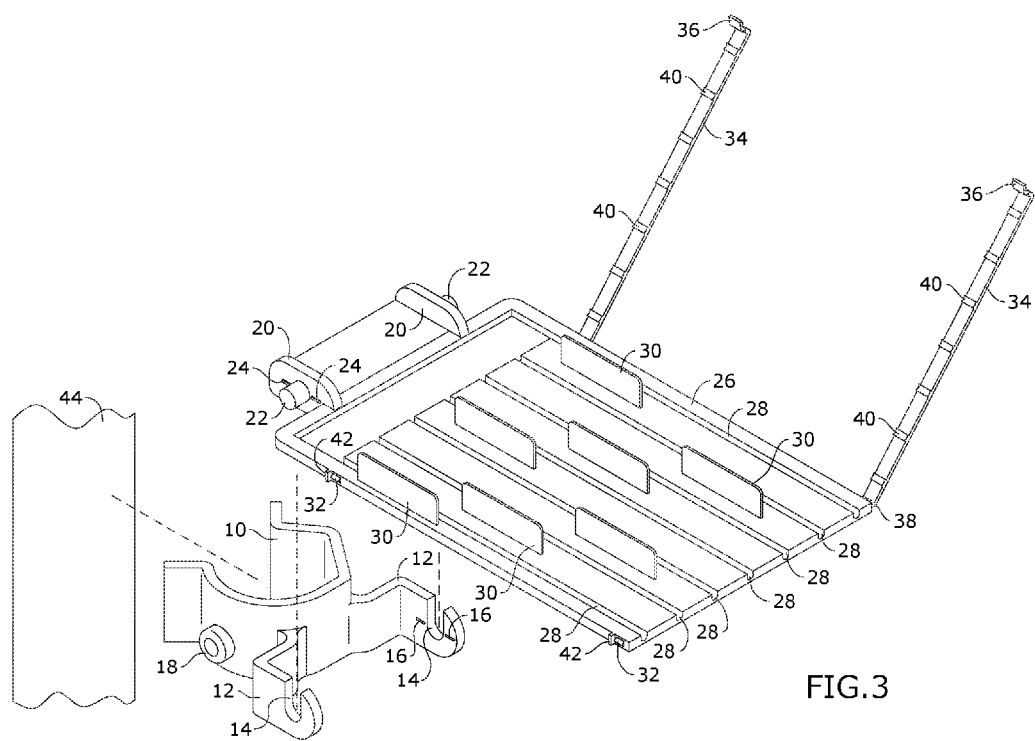
FIG. 3 is an exploded view of one embodiment of the present disclosure.
Figure 4:
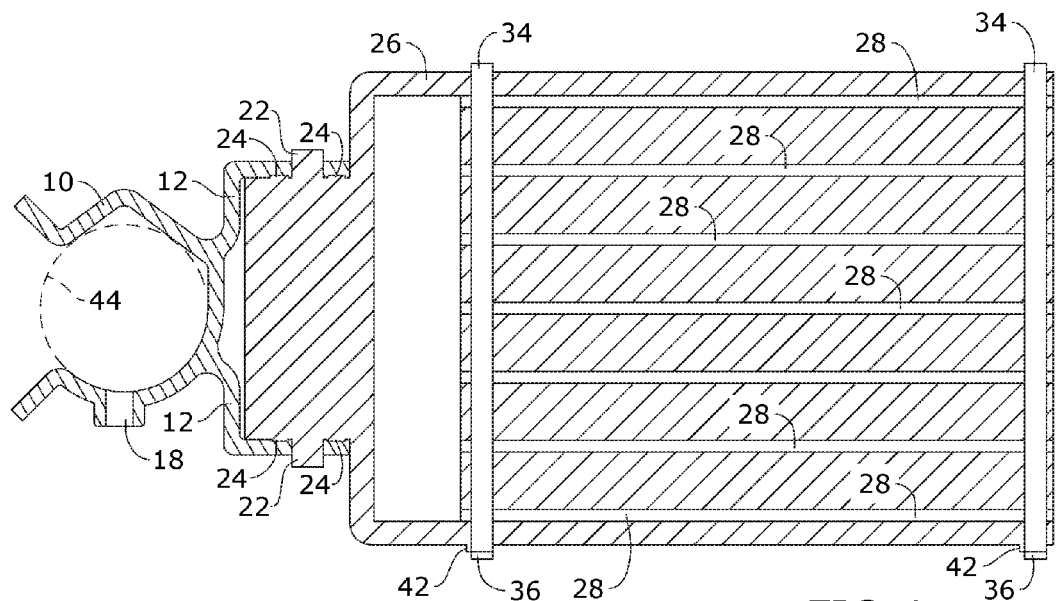
FIG. 4 is a section view of one embodiment of the present disclosure, taken along line 4-4 in FIG. 2.
Figure 5:
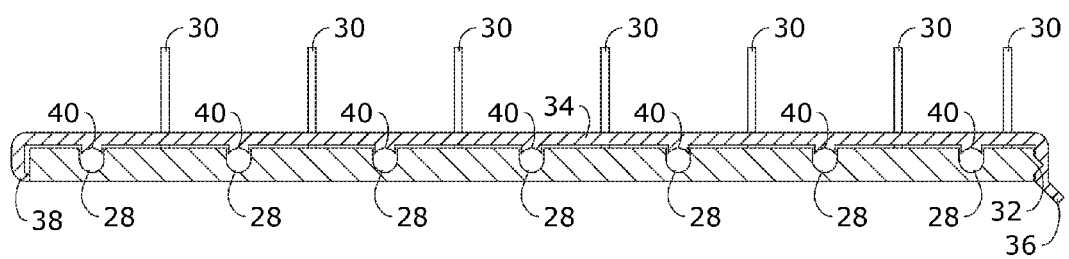
FIG. 5 is a section view of one embodiment of the present disclosure, taken along line 5-5 in FIG. 2.
Figure 6:
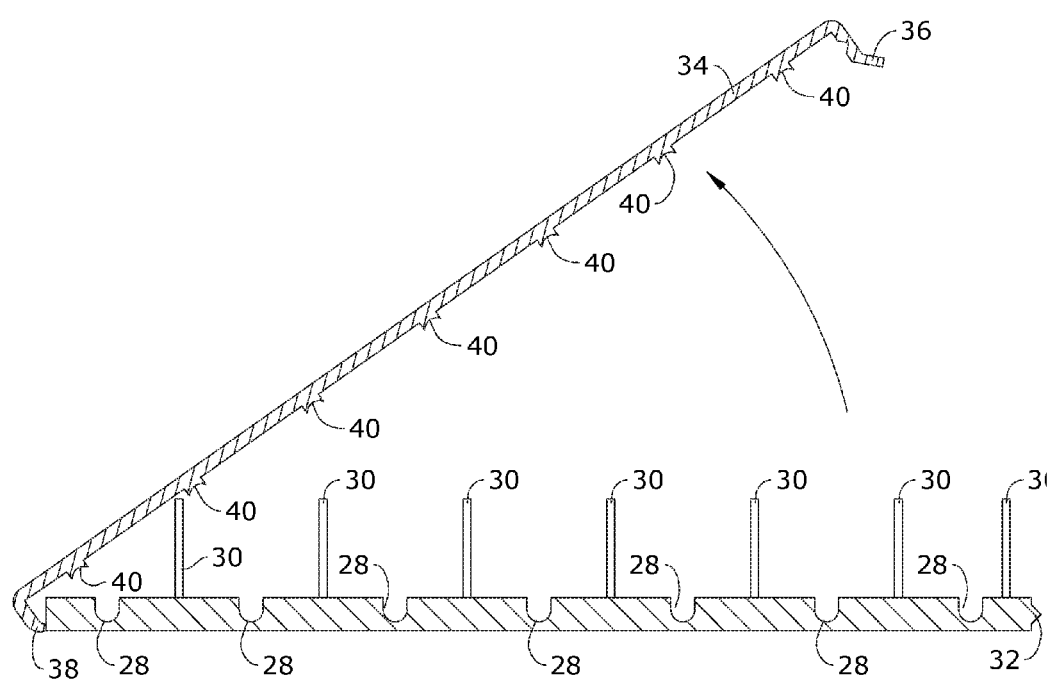
FIG. 6 is a section view of one embodiment of the present disclosure.

By way of example, and referring to FIGS. 1-6, some embodiments of the present disclosure include a device for securing and organizing tubing, such as medical venous access lines, the device comprising a tray 26; a fastener attached to the tray 26, the fastener designed to attach the tray 26 to another object, such as a post 44; at least one tube slot 28 extending partially into the tray 26 and extending from an area of the tray 26 proximate to the fastener to an end of the tray 26 distal from the fastener, the at least one tube slot 28 sized to accommodate at least a portion of a tube 46, such as a venous access line; a first strap 34 attached to the tray 26 proximate to the fastener; and a second strap 34 attached to the tray 26 proximate to the end of the tray 26 distal from the fastener, wherein the first strap 34 and the second strap 34 are designed to clamp down on the tube 46 to secure the tube 46 within the tube slot 28 without impeding flow through the tube 46. In some embodiments, the tray 26 may comprise a plurality of tube slots 28, such as from about 2 to about 10 tube slots 28. In such embodiments, a label tab 30 may extend substantially perpendicularly upwards from the tray 26 proximate to each tube slot 28, such that a user may label each tube 46. As shown in the Figures, each label tab 30 may be substantially rectangular; however, other tab designs are envisioned.

As shown in the Figures, the strap 34 may be hingeably attached to the tray 26 at hinge point 38. Thus, the strap 34 may be opened and closed to reconfigure tubes 46 positioned within the tube slots 28. A bottom surface of the strap 34 (i.e., the surface of the strap 34 facing the tray 26) may comprise at least one tube grip 40. Specifically, the bottom surface of the strap 34 may comprise the same number of tube grips 40 as tube slots 28 in the tray 26. The tube grips 40 may be positioned to align with the tube slots 28 when the strap 24 is closed, such that the tube grips 40 help secure the tubes 46 in place. An edge of the tray 26 opposite the hinge point 38 may have a strap catch 32 extending therefrom. The strap catch 32 may be designed to engage with a strap lift tab 36 on an end of the strap 34 distal from the hinge point 38. Thus, the strap 34 may snap or otherwise secure into place by the engagement of the strap lift tab 36 with the strap catch 32. The edge of the tray 26 opposite the hinge point 38 may also comprise at least one strap stop 42 adjacent to the strap catch 32, wherein the strap stop 42 may prevent the strap 34 from sliding along a length of the tray 26.

In embodiments, the fastener may comprise any suitable structure for attaching the tray 26 to an external object, such as a post 44. For example, the tray 26 may comprise a pair of tabs 20 extending outwardly from an end thereof. Each of the tabs 20 may have a cylindrical extension 22 extending outwardly therefrom. The fastener may comprise a clip 10 designed to at least partially encircle a post 44, wherein the clip 10 includes a set-screw 18 to tighten the clip 10 to the post 44. A pair of clip forks 12 may extend from the clips 10, wherein each of the clip forks 12 include a rounded slot 14 sized to accommodate the cylindrical extensions 22. An inner surface of each fork 12 may include a notch 16 positioned on either side of the rounded slot 14. An outer surface of each tab 20 may include a nub 24 positioned on either side of the cylindrical extension 22. Thus, the cylindrical extensions 22 may slide downward into the rounded slots 14, causing the nubs 24 to engage with the notches 16, securing the tray 26 to the clip 10. However, the use of other fasteners is also envisioned.

The tray 26 of the present disclosure may be substantially flat and may be made of any suitable material. For example, the tray 26 may comprise a metal, such as aluminum, a plastic, a composite material, or the like. The tray 26 may be any desired size and, in some embodiments, may be adjustable in length, width, or both. For example, trays 26 may be snapped together to provide additional length or width, when needed or desired.

As a result of the structure of the device of the present disclosure, tubes, such as medical venous access lines, may be identified, separated, and organized, while simultaneously being securely fixed to a rack. This may eliminate or reduce the chance of contamination on IV lines while simultaneously cutting down the time necessary for changing IV lines for a patient. Moreover, the number of times needed to access a patient's venous system may be reduced, also reducing discomfort for the patient and the risk of tissue damage. The device could, of course, be used to organize and secure other types of tubes, wires, cords, or the like. For example, the device may be used with central catheter lines or feeding tubes.

To use the device of the present disclosure, the user may attach the tray 26 to a desired object, such as a post 44 on a patient's bed or IV unit, place the IV tubing into the tube slots 28, and clamp the straps 34 down on the tubing. Each tubing may be labeled using the label tabs 30. The top end of the tubing may be connected to the source treatment, and the lower end of the tubing may be attached to the patient's IV port. The IV unit may be used as normal.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A device for securing and organizing tubing, the device comprising:
   a tray;
   a fastener attached to the tray, the fastener designed to attach the tray to another object;
   at least one tube slot extending partially into the tray and extending from an area of the tray proximate to the fastener to an end of the tray distal from the fastener, the at least one tube slot sized to accommodate at least a portion of a tube;
   a first strap attached to the tray proximate to the fastener;
   a second strap attached to the tray proximate to the end of the tray distal from the fastener; and
   a label tab extending upwards from the tray proximate to the at least one tube slot,
   wherein the first strap and the second strap are designed to clamp down on the at least one tube to secure the at least one tube within the tube slot without impeding flow through the tube.

2. The device of claim 1, wherein the tray comprises from about 2 to about 10 tube slots.

3. The device of claim 1, wherein:
   a bottom surface of the first strap comprises at least one tube grip positioned to align with the at least one tube slot when the first strap is closed; and
   a bottom surface of the second strap comprises at least one tube grip positioned to align with the at least one tube slot when the second strap is closed.

4. The device of claim 1, wherein:
   the first strap is attached to the tray at a first hinge point;
   the second strap is attached to the tray at a second hinge point;
   an edge of the tray opposite the first hinge point has a first strap catch extending therefrom;
   an edge of the trap opposite the second hinge point has a second strap catch extending therefrom;
   an end of the first strap distal from the first hinge point comprises a first strap lift tab designed to engage with the first strap catch; and
   an end of the second strap distal from the second hinge point comprises a second strap lift tab designed to engage with the second strap catch.

5. The device of claim 4, wherein a first strap stop is positioned adjacent to the first strap catch and a second strap stop is positioned adjacent to the second strap catch, the first strap stop and the second strap stop designed to prevent the first strap and the second strap, respectively, from sliding along a length of the tray.

6. The device of claim 1, wherein the fastener comprises a clip designed to attach the tray to a post.

7. The device of claim 6, wherein:
   the tray comprises a pair of tabs extending outwardly from an end thereof, each of the tabs comprising a cylindrical extension extending outwardly therefrom;
   the clip is to at least partially encircle the post, wherein the clip includes a set-screw to tighten the clip to the post;
   a pair of clip forks extend from the clip, wherein each of the clip forks includes a rounded slot sized to accommodate the cylindrical extensions;
   an inner surface of each fork comprises a notch positioned on either side of the rounded slot; and
   an outer surface of each tab includes a nub positioned on either side of the cylindrical extension, the nubs being designed to engage with the notches.

* * * * *